United States Patent

Larson et al.

[11] Patent Number: 5,902,892
[45] Date of Patent: May 11, 1999

[54] PREPARATION OF ACYLOXYSILANES

[75] Inventors: Gerald L. Larson, Newtown; Ram L. Chawla, Bensalem, both of Pa.

[73] Assignee: Sivento Inc., Somerset, N.J.

[21] Appl. No.: 08/730,842

[22] Filed: Oct. 17, 1996

[51] Int. Cl.[6] .................................. C07F 7/08; C07F 7/18
[52] U.S. Cl. ............................................................ 556/442
[58] Field of Search ............................................. 556/442

[56] References Cited

U.S. PATENT DOCUMENTS 4,556,725 12/1985 Kanner et al. ........................... 556/442
5,387,706 2/1995 Rasmussen et al. ..................... 556/442
5,567,834 10/1996 Bank et al. .............................. 556/442

*Primary Examiner*—Paul F. Shaver
*Attorney, Agent, or Firm*—Abelman, Frayne & Schwab

[57] ABSTRACT

Acyloxysilanes are prepared by the anhydrous reaction of stoichiometric amounts of a carboxylic acid with a mixture of a halosilane and a silazane in an aprotic solvent, such as diethyl ether, acetonitrile, tetrahydrofuran or toluene, in an inert gas atmosphere. In a preferred embodiment the silazane is prepared in situ by the reaction of the corresponding halosilane and ammonia. No catalyst is necessary and the reaction preferably is performed at a temperature of −5° C. to 45° C.

18 Claims, No Drawings

PREPARATION OF ACYLOXYSILANES

FIELD OF THE INVENTION

The present invention relates to a process for the preparation of acyloxysilanes. Acyloxysilanes are well-known cross-linking agents for one-part room temperature vulcanizable silicone rubber compositions. One such acyloxysilane cross-linking agent is methyltriacetoxysilane.

BACKGROUND OF THE INVENTION

Acyloxysilanes have been prepared by the reaction of an alkylchlorosilane with a carboxylic acid. The reaction is reversible and is brought to completion by removing the by-product HCl either by addition of a proton acceptor or by distilling it off at high temperature. The reaction mechanism can be represented as follows:

$$R_nSiCl_{4-n}+(4-n)CH_3COOH \rightarrow R_nSi(OCOCH_3)_{4-n}+(4-n)HCl \quad (I)$$

where R is an alkyl radical and n is an integer from 0 to 3.

The reaction scheme of (I) is the subject of various methods for improving the yield of the desired end product, including the addition of an iron complexing agent, (U.S. Pat. No. 3,974,198); conducting the reaction under reflux conditions using pentane as a solvent (U.S. Pat. No. 4,028, 391); conducting the reaction in the vapor phase in a counter-current column (U.S. Pat. Nos. 4,329,484 and 4,332, 956); and refluxing the reactants in carbon tetrachloride as a solvent (Japanese patent document 80,154,983 (1980)).

These reaction schemes have the disadvantages of requiring either (1) additional reactants to neutralize or otherwise remove the HCl, or (2) additional utilities and equipment to conduct the reaction and to remove the HCl from the reactor in order to drive the reaction to completion.

Alkylacyloxsilanes have also been obtained by the reaction of a carboxylic acid anhydride with an alkylchlorosilane:

$$R_nSiCl_{4-n}+(4-n)(CH_3CO)_2O \rightarrow R_nSi(OCOCH_3)_{4-n}+(4-n)CH_3COCl \quad (II)$$

where R is an alkyl radical and n is an integer from 0 to 3.

This reaction (II) is brought to completion by distilling off the acetyl chloride formed. Acetyl chloride is corrosive, toxic, a strong irritant and presents a significant fire risk. It must be handled carefully and disposed of properly. A modification of this process is disclosed in European patent EP 509,213.

The technical literature also discloses other processes relating to specific acyloxysilanes. For example, Hengge, E. and Starz, E. (Montash. Chem. 102(3) 741–6 1971; CA 75, 88066) reported the preparation of triacetoxysilane (11.8% yield) by treating trichlorosilane with sodium acetate in pentane at room temperature. Kohma S. and Matsumoto, S. (Kagaku To Kogyo (Osaka) 48(8) 308–10 1974; CA 82 57798) improved the yield (48–64%) in the preparation of alkylacetoxysilanes by refluxing the chlorosilanes with magnesium acetate in benzene. The use of a metal salt of the acid in these processes results in production of a metal chloride, either NaCl or $MgCl_2$, which requires additional washing steps for product recovery.

It is therefore a principal object of the present invention to provide an improved one-step process for the production of acyloxysilanes by reacting a halosilane with other relatively inexpensive reactants.

It is another object of the present invention to provide an improved process for producing acyloxysilanes at moderate temperatures in the range from about −5° C. to about 50°.

Another object of this invention is to provide a process for the production of acyloxysilanes that does not require a catalyst.

A further object of this invention is to provide a process for the production of acyloxysilanes that does not require a high-temperature distillation process and that can be carried out in conventional reactors.

It is also an important object of the invention to provide a process in which the acyloxysilanes are obtained in yields exceeding at least 75%, and up to 95%.

It is an additional object of the present invention to provide an improved process for the production of acyloxysilanes in which the by-products are non-hazardous and can readily be disposed of in accordance with existing environmental regulations.

Still another object of the present invention is to provide a process for producing acyloxysilanes in which the solvent can be recycled, and where the acyloxysilane remaining in the reaction vessel after removal of the solvent is sufficiently pure so that it can be used without further purification.

SUMMARY OF THE INVENTION

In accordance with the method of the invention, the acyloxysilanes are prepared by the reaction of a carboxylic acid and a mixture of a halosilane and a silazane. The reaction can be conducted using stoichiometric quantities of the respective reactants based upon the following reaction scheme:

$$[R_nSi]_a[(NH)_{(4-n)}]_a[SiR_n]_a+aR_nSiX_{(4-n)}+3a(4-n)R'COOH \rightarrow 3aR_n\text{-}Si(OCOR')_{(4-n)}+a(4-n)NH_4X \quad (III)$$

where R and R' are alkyl or aryl having 1 to 20 carbon atoms, X is halogen, n is an integer from 0 to 3 and a is 1–20.

In carrying out the process of the invention, the ratio of the Si—Cl substituents of the halosilane compound to the Si—NH substituents of the silazane should be in the ratio of 1:2. The preferred compounds are those where a is 1, 3 or 4.

Silazanes that can be utilized in the reaction include, but are not limited to the following: hexamethyldisilazane, 1,3 diphenyltetramethyldisilazane, 1,3-divinyltetramethyldisilazane, hexamethylcyclotrisilazane and octamethylcyclotetrasilazane.

In a preferred embodiment, the silazane is prepared in situ by the reaction of anhydrous ammonia with the corresponding halosilane. The latter reaction can be represented as follows:

$$2aR_nSiX_{4-n}+3a(4-n)NH_3 \rightarrow [R_nSi]_a[(NH)_{4-n}]_a[SiR_n]_a+2a(4-n)NH_4X \quad (IV)$$

where R and R' are alkyl or aryl radicals of from 1 to 20 carbons atoms, n is an integer from 0 to 3, a is from 1–20 and X is a halogen.

Preferred alkyl constituents are methyl ethyl, n-propyl and vinyl. A preferred aryl is phenyl.

In order to maximize the yield of the desired acyloxysilane and minimize byproducts, the reaction is conducted in an aprotic solvent. Criteria for selecting the aprotic solvent include cost, the relative ease of handling the solvent and its boiling point, since the desired product is preferably recovered by distilling off the solvent. Suitable solvents include toluene, diethyl ether, tetrahydrofuran and acetonitrile, with diethyl ether and toluene being preferred.

In the practice of the invention illustrated by reaction (IV), the initial temperature of the reactants in the vessel is lowered in order to facilitate the absorption and retention of the gaseous ammonia in the solvent. The greater the concentration of ammonia dissolved in the reaction medium, the more efficiently will the reaction proceed. In addition, conducting the reaction at a relatively lower temperature results in relatively fewer side reactions.

EXAMPLE 1

Preparation of Methyltriacetoxysilane

Two hundred and sixty grams (1.7 mol) of methyltrichlorosilane and 750 ml of diethyl ether were added to a dry reaction vessel fitted with a thermometer and a gas inlet tube under a dry nitrogen atmosphere and stirred. The vessel was then cooled to a temperature of 0° C. and charged with a 89 g (5.23 mol) of anhydrous ammonia over a period of one hour. During the addition of ammonia, the reaction mixture was allowed to warm to 5° C. After the addition of the ammonia, the reaction mixture was stirred at a temperature of approximately 25° C. for 30 minutes. The gas inlet tube was replaced by the addition funnel and acetic acid 314 g (5.23 mol) was added to the reaction mixture over a period of one hour. During the addition of acetic acid, the reaction mixture was refluxing at a pot temperature of 41° C. After the addition of acetic acid, the reaction mixture was refluxed for 30 minutes and then cooled to room temperature. The methyltriacetoxysilane was filtered under a nitrogen atmosphere from the ammonium chloride. The ammonium chloride was washed with ether (2×200 ml) to obtain residual methyltriacetoxysilane. At this stage, analysis of the product showed diethyl ether (4.7%), methyltriacetoxysilane (73.6%) and higher boiling components (15.8%).

The solvent was initially removed by distillation to a pot temperature of 70° C. The residue was distilled under vacuum to provide 290 g of methyltriacetoxysilane as colorless oil, bp 87° C./3 mm, having a purity greater than 98%. The yield was 77% of theoretical.

EXAMPLE 2

Preparation of Methyltriacetoxysilane

The procedure of Example 1 was followed, except that toluene was substituted for diethyl ether as the solvent. The reaction mixture was heated to 60° C. for 30 minutes to complete the reaction. The residue left after filtration and removal of the solvent was distilled under reduced pressure to provide methyltriacetoxysilane having a purity of 98.5%. The yield was 78% of theoretical.

EXAMPLE 3

Preparation of Ethyltriacetoxysilane

One hundred and ninety-eight grams (1.21 mol) of ethyltrichlorosilane and one liter of diethyl ether were added to a dry reaction vessel fitted with a thermometer and a gas inlet tube under a dry nitrogen atmosphere and stirred. The vessel was then cooled to a temperature of 5° C. and charged with a 93 g (5.47 mol) of anhydrous ammonia over a period of one hour. During the addition of ammonia, the reaction mixture was allowed to warm to 15° C. After the addition of the ammonia, the reaction mixture was stirred at a temperature of approximately 25° C. for 30 minutes. The gas inlet tube was replaced by the addition funnel and 99 g (0.605 mol) of ethyltrichlorosilane was added to the stirred reaction mixture. Thereafter, 329 g (5.47 mol) of acetic acid was added over a period of one hour. During the addition of acetic acid, the reaction mixture was refluxed at a pot temperature of 41° C. After the addition of acetic acid, the reaction mixture was refluxed for 30 minutes and then cooled to room temperature. The ethyltriacetoxysilane was filtered under a nitrogen atmosphere from the ammonium chloride. The ammonium chloride was washed with diethyl ether (2×200 ml) to obtain the residual ethyltriacetoxysilane. The solvent was removed by distillation to a pot temperature of 70° C. The residue was distilled under reduced pressure to provide 334 g of ethyltriacetoxysilane as colorless oil, bp 107° C. at 8 mm. The yield was 81% of theoretical.

In the examples which follow, the acyloxysilane is prepared by the reaction of an alkylhalosilane with a silazane.

EXAMPLE 4

Preparation of Trimethylsilyl Acetate

A thermometer, an addition funnel and a condenser were fitted to a stirrer-equipped one liter four-necked flask. The flask was charged with 109 g (1 mol) of trimethychlorosilane and 161.5 g (1 mol) of hexamethyldisilazane and stirred. The vessel was cooled to a temperature of 20° C. and charged with a 180 g (3 mol) of acetic acid over a period of 30 minutes. During the addition of the acetic acid, the reaction mixture was allowed to warm to 45° C. After the addition of the acetic acid, the reaction mixture was stirred at a temperature of approximately 25° C. for 30 minutes. The trimethylsilyl acetate was filtered under a nitrogen atmosphere from the ammonium chloride.

The ammonium chloride was washed with ether (2×100 ml) to obtain residual trimethylsilyl acetate. The solvent was removed by distillation to provide 365 g of trimethylsilyl acetate as a colorless oil having a purity of 98%. The yield was 92% of theoretical.

EXAMPLE 5

Preparation of Dimethyldiacetoxysilane

A thermometer, an addition funnel and a condenser were fitted to a stirrer-equipped one liter four-necked flask. The flask was charged with 55 g (0.251 mol) of hexamethylcyclotrisilazane, 48.5 g (0.376 mol) of dimethyldichlorosilane and 250 mL of diethyl ether under a dry nitrogen atmosphere and stirred. To this charge was added 135.5 g (2.26 mol) of acetic acid over a period of one hour. During the addition of the acetic acid, the reaction mixture was refluxing at a pot temperature of 42° C. After the addition of the acetic acid, the reaction mixture was stirred at a temperature of approximately 25° C. for 30 minutes.

The dimethyldiacetoxysilane was filtered under a nitrogen atmosphere from the ammonium chloride crystals. The solid ammonium chloride was washed with ether (2×50 mL) to obtain the residual dimethyldiacetoxysilane. The solvent was removed by distillation. The residue, (having a purity of about 95%) was distilled under vacuum to provide 181 g of dimethyldiacetoxysilane as a colorless oil (bp 72° C./36 mm.) The purity of the product exceeded 98%. The yield was 91% of theoretical.

EXAMPLE 6

Preparation of Trimethylsilyl Cyanoacetate

A thermometer, an addition funnel and a condenser were fitted to a stirrer-equipped 500 mL four-necked flask. The flask was charged with 58.6 g (0.69 mol) of anhydrous cyanoacetic acid in 50 mL of tetrahydrofuran under a dry nitrogen atmosphere and stirred. To this was added a mixture of 25.0 g (0.23 mol) of trimethylchlorosilane and 37.2 g (0.23 mol) of hexamethyldisilazane over a period of 30 minutes. During the addition of the latter mixture, the reaction mixture was allowed to warm to 45° C. and thereafter, the reaction mixture was cooled and stirred at a temperature of approximately 35° C. for about 30 minutes.

The trimethylsilyl cyanoacetate was filtered under a nitrogen atmosphere from the ammonium chloride. The crystalline ammonium chloride was washed with tetrahydrofuran (2×15 mL) to obtain the residual trimethylsilyl cyanoacetate. The solvent was removed by distillation and 98.0 g of trimethylsilyl cyanoacetate in the form of a colorless oil (bp 51° C. at 0.25 mm) having a purity of 98.7% was isolated on distillation under reduced pressure. The yield was 90% of theoretical.

We claim:

1. A process for the production of acyloxysilane according to reaction (III), where R and R' are alkyl or aryl having one to twenty carbon atoms, X is halogen, n is an integer from 0 to 3 and a is 1–20.

2. The process of claim 1 where the reaction is conducted in an aprotic solvent.

3. The process of claim 2 where the solvent is tetrahydrofuran, diethyl ether, toluene or dimethylformamide.

4. The process of claim 3 where the solvent is diethyl ether.

5. The process of claim 2 where the reaction is conducted batchwise and the solvent is recovered for use in subsequent batches.

6. The process of claim 3 where the acyloxysilane end product is recovered after distillation of the solvent.

7. The process of claim 1 where X is chlorine.

8. The process of claim 1 where the reaction is conducted at a temperature in the range from about −5° C. to about 50° C.

9. The process of claim 1 where the reaction is conducted at least in part in the absence of oxygen.

10. The process of claim 9 where the reaction is conducted at least in part in a nitrogen atmosphere.

11. The process of claim 1 where ammonia is added in the form of a gas to the halosilane at a temperature ranging from about −5° C. to about 60° C. to form the silazane in situ.

12. The process of claim 1 where the reaction mixture is maintained at a temperature ranging from about 40° C. to about 45° C. following addition of the acid.

13. A process for the production of acyloxysilane of the formula $R_nSi(OCOR')_{(4-n)}$, where R and R' are alkyl or aryl radicals having 1 to 20 carbon atoms, n is an integer from 1 to 3, and X is a halogen, where the process comprises the steps:

(a) forming a mixture of stoichiometric amounts of a halosilane having the formula $R_nSiX_{(4-n)}$ with a silazane of the formula

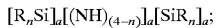

$[R_nSi]_a[(NH)_{(4-n)}]_a[SiR_n]_a;$ (b) adding to the mixture of step (a) a stoichiometric amount of a monocarboxylic acid of the formula R'COOH;

(c) agitating the reaction mixture in an aprotic solvent for a time sufficient to produce the desired $R_nSi(OCOR')_{(4-n)}$ and $NH_4X$;

(d) separating the acyloxysilane from the $NH_4X$; and (e) recovering the acyloxysilane from the solvent.

14. The process of claim 13 which further comprises the step of adding gaseous ammonia to the halosilane of step (a) to form the silazane in situ.

15. The process of claim 14 where the reaction is conducted in a nitrogen atmosphere.

16. The process of claim 13 where the acyloxysilane is separated from the solvent by distillation.

17. The process of claim 13 where R and R', or both of them, are selected from the group consisting of linear or branched chain alkyl groups having from 1 to 20 carbon atoms, aryl groups having from 6 to 20 carbon atoms and aralkyl groups having up to 20 carbon atoms.

18. The process of claim 13 where X is chlorine.

* * * * *